United States Patent [19]

Appel et al.

[11] Patent Number: 5,471,002

[45] Date of Patent: Nov. 28, 1995

[54] PROCESS FOR PREPARING TRIFLUOROMETHYLANILINES

[76] Inventors: Wolfgang Appel, Taunusstrasse 74a, D-65779 Kelkheim; Günter Siegemund, Frankfurter Strasse 21, D-65719 Hofheim, both of Germany

[21] Appl. No.: 292,723

[22] Filed: Aug. 18, 1994

[30] Foreign Application Priority Data

Aug. 20, 1993 [DE]  Germany .................. 43 28 028.5

[51] Int. Cl.⁶ .................................. C07C 209/22
[52] U.S. Cl. .................. 564/412; 564/394; 564/415; 558/418; 558/420
[58] Field of Search ................... 564/393, 394, 564/414, 415, 412, 114; 558/416, 419, 418

[56] References Cited

U.S. PATENT DOCUMENTS

| | | | |
|---|---|---|---|
| 4,481,370 | 11/1984 | Lin et al. | 564/394 |
| 4,748,277 | 5/1988 | Desbois | 564/414 |

FOREIGN PATENT DOCUMENTS

| | | | |
|---|---|---|---|
| 0152310 | 7/1987 | European Pat. Off. | |
| 955898 | 4/1964 | United Kingdom | |

OTHER PUBLICATIONS

European Search Report No. 94112737, Dec. 19, 1994.
Journal of Fluorine Chemistry, vol. 52, No. 2, Apr. 15, 1991, pp. 107–116.

Primary Examiner—Richard L. Raymond
Assistant Examiner—Brian M. Burn
Attorney, Agent, or Firm—Connolly and Hutz

[57] ABSTRACT

A process for preparing trifluoromethylanilines of the formula (I),

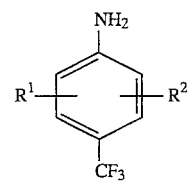

in which $R^1$ and $R^2$, independently of each other, are hydrogen, halogen, ($C_1$–$C_4$) alkyl, hydroxyl, alkoxy, alkylthio, carboxyl, or a nitro or cyano group, by reacting compounds of the formula (II)

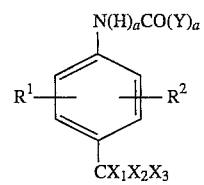

in which $X_1$, $X_2$ and $X_3$ are in each case, identically or differently, halogen atoms, a is 0 or 1, Y is fluorine, chlorine or bromine, and $R^1$ and $R^2$ have the defined meaning, with anhydrous hydrofluoric acid, and converting the resulting aniline hydrofluorides with a base into the free amines.

14 Claims, No Drawings

PROCESS FOR PREPARING TRIFLUOROMETHYLANILINES

DESCRIPTION

The present invention relates to a process for preparing 4-trifluoromethylanilines.

Trifluoromethylanilines, and 4-trifluoromethylanilines in particular, are valuable intermediates for synthesizing active compounds in the pharmaceutical and plant-protection fields.

L. P. Seiwell (J. Org. Chem. 44, 4731 to 4733 (1979)) has described the preparation of p-trifluoromethylaniline from 4-chlorotrifluoromethylbenzene by aminolysis in the presence of copper(I)chloride and potassium fluoride. However, the conversions are low and the yields are, correspondingly, too small for an industrial process.

Some processes have also been described for preparing p-trifluoromethylaniline by reducing the corresponding nitro precursor (e.g. J. Org. Chem. 26, 1477 to 1480 (1961), J. Amer. Chem. Soc. 69, 2346 to 2350 (1947)). However, 4-nitrotrifluoromethylbenzene is very difficult to obtain since the nitration of benzotrifluoride yields the m-compound practically exclusively (> 96%).

A method has also been described for using free-radical addition of trifluoromethyl bromide to electron-rich aromatic compounds in order to obtain the corresponding trifluoromethylaryl derivatives (J. Chem. Soc., Perkin 1, 2293 to 2299 (1990)). However, the reaction has a low positional selectivity and also provides only moderate yields. Other methods described in the recent literature are similarly unsuitable for industrial use owing to the fact that they employ very expensive reagents (Tetrahedron Lett. 31, 3579 to 3582 (1990)) or elaborate reaction steps (J. Org. Chem. 54, 2873 to 2877 (1989)).

Two processes have also been described which proceed from p-trichloromethylphenyl isocyanate. In the older patent (FR 1 545 142), the trichloromethyl group is first converted, in hydrofluoric acid, into the trifluoromethyl group, and the trifluoromethylphenyl isocyanate is then transferred, in an elaborate manner, into an organic solvent and the isocyanate grouping is finally hydrolyzed with conc. (98%) sulfuric acid.

In the more recent patent (EP 0 152 310), the process was simplified to the effect that the chlorine/fluorine exchange and the hydrolysis are carried out in one step by adding a set (at least molar) quantity of water to the hydrofluoric acid, and the working-up of the reaction mixture is carried out in a defined manner.

On the other hand, it is known from the more recent literature (Lin, Cotter, Bieron, Krishnamurti, J. Fluorine Chem. 52, 107 to 116 (1991)) that the hydrofluoride of 2-trifluoromethylaniline is formed directly, in anhydrous hydrofluoric acid and with the generation of carbonyl fluoride, from 2-trichloromethylphenyl isocyanate in a previously unknown solvolysis reaction. However, the use of the same reaction conditions on phenyl isocyanate and p-trifluoromethylphenyl isocyanate resulted to a large extent in the formation of the corresponding diarylureas, something which, in the case of the ortho-substituted derivatives, is prevented for steric reasons. While U.S. Pat. No. 4,481,370 discloses that it is possible to convert various phenylcarbamoyl fluorides into the arylamine hydrofluorides at room temperature or at elevated temperature when the phenylcarbamoyl fluorides are previously produced from the phenyl isocyanates at low temperatures (around 0° C.), it is nevertheless reported in that publication that it is necessary to add water in order to achieve acceptable reaction times. In addition to this, the yields which are reported—except in the case of 2-trifluoromethylaniline— are too low for the process to appear attractive from the point of view of ecology and economy.

Owing to the general importance of this class of compounds, and the many uses to which they can be put, it is a worthwhile object to provide a novel process for synthesizing these compounds, which avoids the disadvantages described and is simple to carry out on an industrial scale.

The object is achieved by a process for preparing p-trifluoromethylanilines of the formula (I),

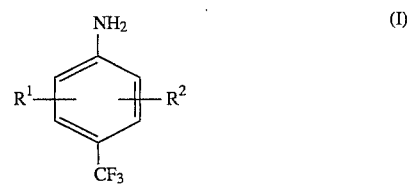

in which
$R^1$ and $R^2$, independently of each other, are hydrogen, halogen, ($C_1$–$C_4$) alkyl, hydroxyl, alkoxy, alkylthio, carboxyl, or a nitro or cyano group, wherein compounds of the formula (II)

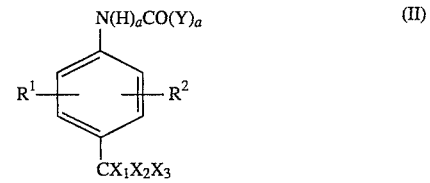

in which
$X_1$, $X_2$ and $X_3$ are in each case, identically or differently, halogen atoms,
a is 0 or 1,
Y is fluorine, chlorine or bromine, and
$R^1$ and $R^2$ have the defined meaning, are reacted with anhydrous hydrofluoric acid and the resulting aniline hydrofluorides are converted with a base into the free amine.

It has been found, surprisingly, that halogen/fluorine exchange and solvolysis of the isocyanate group also take place with p-trihalomethylphenyl isocyanates in anhydrous hydrofluoric acid to form the 4-trifluoromethylphenylaniline hydrofluorides in one step and in excellent yields. After having distilled off the anhydrous hydrofluoric acid, the latter compounds can be converted into the free amine by simple neutralization. In contrast to the abovementioned patent (EP 0 152 310), the present process avoids the addition of water to the hydrofluoric acid, as a consequence of which the latter can be recycled without difficulty and, with the exception of the equivalents which are required for the reaction, almost completely. In our case, the neutralization can also be carried out simply using potassium hydroxide, which offers considerable technical advantages as compared with the potassium carbonate employed in the above patent. In addition to phenyl isocyanates, the corresponding phenylcarbamoyl halides are also suitable for use as starting compounds, the latter halides being converted in situ into the phenylcarbamoyl fluorides—in so far as the carbamoyl fluoride is not employed directly— and then subjected to the same solvolysis step.

The process is ecologically very advantageous since the hydrofluoric acid can be recycled almost quantitatively.

While the process can be carried out using all trihalomethyl derivatives, the use of the corresponding trichloro compounds is of particular industrial interest.

4-Trichloromethylphenyl isocyanate, 2-chloro-4-trichloromethylphenyl isocyanate, 2,6-dichloro-4-trichloromethylphenyl isocyanate, and the corresponding carbamoyl halides, are very interesting starting compounds.

While, for implementing the reaction in accordance with the invention, at least five times the molar quantity of hydrofluoric acid must be used per mole of isocyanate or carbamoyl halide, from 10 to 40 equivalents are preferably employed, something which does not present any difficulty owing to the fact that anhydrous hydrofluoric acid can be readily recycled.

In general, the reaction is allowed to proceed at temperatures of between 20° and 130° C. In many cases, it has proved worthwhile to operate at from 20° to 80° C., in particular at between 35° and 70° C. The duration of the reaction depends on the substrate and on the reaction temperature and is between 0.5 and 5 hours.

Pressure vessels made of stainless steel or other suitable materials are used as reaction vessels, which should be provided with a reflux condenser and a valve situated downstream thereof in order to facilitate the exhausting of hydrogen chloride and carbonyl fluoride during the reaction.

Once the reaction has finished, hydrogen chloride and carbonyl fluoride are first exhausted completely. The excess anhydrous hydrofluoric acid, which can be reused without further purification, is then distilled off as completely as possible at about 30° C. After opening the autoclave, the reaction mixture can be removed as such or first transferred into solution by adding a suitable solvent such as ethyl acetate, methylene chloride, methyl t-butyl ketone, toluene, or the like.

The free aniline is obtained from the reaction mixture present in one of the above listed solvents after adjusting the pH to a value of between 8 and 10, and can then be isolated in high yields by simple distillation.

The following examples serve to illustrate the process according to the invention without, however, limiting it to these examples.

EXAMPLES

1) 4-Trifluoromethylaniline 236 g (1 mol) of 4-trichloromethylphenyl isocyanate are initially introduced into a 2 l stainless steel autoclave, which has previously been dried in a stream of inert gas and which possesses a stirrer, a reflux condenser and a shut-off valve situated over the latter, and 600 g (30 mol) of anhydrous hydrofluoric acid (water content< 0.1%) are then added.

The mixture is now heated at 70° C. for 4 hours. During the reaction period, the shut-off valve is opened from time to time and the internal pressure is on each occasion lowered to about 10 bar by exhausting hydrogen chloride and carbonyl fluoride.

At the end of the reaction period, the autoclave is allowed to cool to an internal temperature of between 30° and 35° C. and the hydrofluoric acid is exhausted as completely as possible at this temperature. Once the reactor has been opened, the reaction mixture is dissolved in 500 ml of ethyl acetate and transferred into a mixing vessel into which 500 ml of an ice/water mixture have been initially introduced. While stirring vigorously, the pH of the mixture is adjusted to between 8 and 10 by adding a 30% aqueous solution of potassium hydroxide. The upper organic phase is then separated off and washed once in each case with water and a solution of sodiumchloride and dried over sodium sulfate. Fractional distillation in vacuo yields 135 g (83.8% of theory) of 4-trifluoromethylaniline (boiling point, 86° C./14 mmHg), the purity (GC>99.8%) and identity of which were examined.

($^1$H NMR (CDCl$_3$): δ=7.3, 2 H, d=8.7 Hz; δ=6.6, 2H, d=8.7 Hz; δ=3.9 br s, 2 H)

2) 2-Chloro-4-trifluoromethylaniline 135 g (0.5 mol) of 2-chloro-4-trichloromethylphenyl isocyanate and 500 g of anhydrous HF are reacted at 70° C. for 4 hours in a pressure vessel in the same manner as in Example 1 and subsequently worked up in a completely analogous manner. The product (76 g, 78% of theory) is once again obtained by fractional distillation. Its identity and purity were demonstrated by GC/NMR ($^1$H NMR (CDCl$_3$): δ=7.5, 1 H, br s; δ=7.2, 1 H, br s; δ=6.6, 1 H, d, 8.6 Hz; δ=4.35, 2 H, br s).

3) 2,6-Dichloro-4-trifluoromethylaniline 151.1 g (0.5 mol) of 2,6-dichloro-4-trichloromethylaniline are treated with 500 g of anhydrous hydrofluoric acid at 70° C. for 5 hours in the same manner as in Example 1. Following analogous working-up, the desired product is obtained in good yield (81 g, 70% of theory) by fractional distillation. Its identity was examined by spectra and melting point (from 35° to 36° C.).

We claim:

1. A process for preparing trifluoromethylanilines of the formula (I),

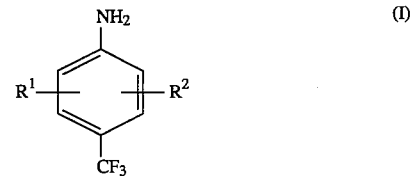

in which

R$^1$ and R$^2$, independently of each other, are hydrogen, halogen, (C$_1$–C$_4$)alkyl, hydroxyl, alkoxy, alkylthio, carboxyl, or a nitro or cyano group, wherein compounds of the formula (II)

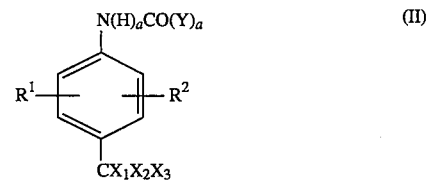

in which

X$_1$, X$_2$ and X$_3$ are in each case, identically or differently, halogen atoms, a is 0 or 1, Y is fluorine, chlorine or bromine, and R$^1$ and R$^2$ have the defined meaning, are reacted with anhydrous hydrofluoric acid and the resulting aniline hydrofluorides are converted with a base into the free amine.

2. The process as claimed in claim 1, wherein a is 0 in formula (II).

3. The process as claimed in claim 1, wherein $X_1$, $X_2$ and $X_3$ are chlorine atoms in formula (II).

4. The process as claimed in claim 1, wherein $R^1$ and $R^2$ are hydrogen or chlorine in formula (II).

5. The process as claimed in claim 1, wherein formula (II) represents 4-trichloromethylphenyl isocyanate.

6. The process as claimed in claim 1, wherein the molar ratio of anhydrous hydrofluoric acid to the compound of the formula (II) is between 5 and 50.

7. The process as claimed in claim 1, wherein the reaction with anhydrous hydrofluoric acid is carried out at a temperature of from 20° to 130° C.

8. The process as claimed in claim 1, wherein an alkali metal hydroxide is used as the base.

9. The process as claimed in claim 1, wherein the anhydrous hydrofluoric acid is recycled.

10. The process as claimed in claim 1, wherein the molar ratio of anhydrous hydrofluoric acid to the compound of the formula II is between 10 and 40.

11. The process as claimed in claim 1, wherein the reaction within anhydrous hydrofluoric acid is carried out at a temperature of from 20° to 80° C.

12. The process as claimed in claim 1, wherein the reaction within anhydrous hydrofluoric acid is carried out at a temperature of between 35° and 70° C.

13. The process as claimed in claim 1, wherein potassium hydroxide is used as the base.

14. A process for the preparation of trifluoromethylaniline of the formula (I)

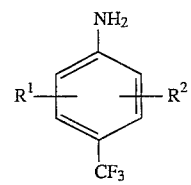

in which
$R^1$ and $R^2$, independently of each other, are hydrogen, halogen, $C_1$–$C_4$ alkyl, hydroxy, alkoxy, alkylthio, carboxyl, or a nitro or cyano group, comprising the steps of:

reacting a compound of the formula II

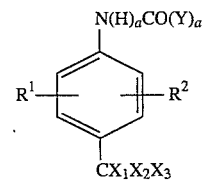

in which
$X_1$, $X_2$, and $X_3$ are in each case identically or differently, halogen atoms,
a is 0 or 1, and
Y is fluorine, chlorine, or bromine, with anhydrous hydrofluoric acid in an anhydrous environment to form aniline hydrofluoride,
removing the hydrofluoric acid, and
converting the aniline hydrofluoride with a base to a free amine.

* * * * *